United States Patent
Kazmierczak et al.

(10) Patent No.: US 7,563,236 B2
(45) Date of Patent: Jul. 21, 2009

(54) SHOULDER SLING WITH SUPPORT PILLOW AND POUCH

(75) Inventors: Andy Kazmierczak, Oceanside, CA (US); Stephen J. Snyder, Van Nuys, CA (US); Eric McCarty, Lafayette, CO (US); Colin S. Gregersen, Cardiff, CA (US); Nancy Halchuk, Vista, CA (US); Alfredo Cesena, Tijuana (MX)

(73) Assignee: DJO, LLC, Vista, CA (US)

( * ) Notice: Subject to any disclaimer, the term of this patent is extended or adjusted under 35 U.S.C. 154(b) by 289 days.

(21) Appl. No.: 10/663,381

(22) Filed: Sep. 15, 2003

(65) Prior Publication Data

US 2005/0010147 A1 Jan. 13, 2005

(51) Int. Cl.
*A61F 5/01* (2006.01)

(52) U.S. Cl. ......................................................... 602/4

(58) Field of Classification Search ................... 602/5, 602/16, 20, 4, 3, 19, 13; 128/77, 878; 5/648, 5/646, 630, 922, 933, 636, 907; 224/157, 224/158

See application file for complete search history.

(56) References Cited

U.S. PATENT DOCUMENTS

| | | | |
|---|---|---|---|
| 2,310,556 A | | 2/1943 | Anderson |
| 3,404,680 A | * | 10/1968 | Guttman et al. ............... 602/4 |
| 3,788,308 A | | 1/1974 | Simpson |
| 4,180,870 A | | 1/1980 | Radulovic et al. |
| 4,372,301 A | | 2/1983 | Hubbard et al. |
| 4,598,701 A | | 7/1986 | Schaefer |
| 4,617,923 A | | 10/1986 | Coleman |
| 4,622,961 A | | 11/1986 | Christensen |
| 4,625,719 A | | 12/1986 | Chambers |
| 4,716,895 A | * | 1/1988 | Marques et al. ............... 602/4 |
| 4,834,082 A | | 5/1989 | Ghadiali |
| 4,896,660 A | | 1/1990 | Scott |
| D317,840 S | * | 7/1991 | Jagdat .......................... D6/601 |
| 5,334,132 A | | 8/1994 | Burkhead |

(Continued)

FOREIGN PATENT DOCUMENTS

EP    362528  A1 *  4/1990

(Continued)

OTHER PUBLICATIONS

Author Unknown, Upper Extremity Bracing depicting the Slingshot, Adjustable Sling and Shoulder Abduction Pillow, Breg © Product Catalog 2002, 1 page.

(Continued)

*Primary Examiner*—Danton DeMille
(74) *Attorney, Agent, or Firm*—Ropes & Gray LLP (57) ABSTRACT

A shoulder sling is provided for the treatment of, for example, gleno-humeral dislocations and subluxations, capsular shifts, postoperative rotator cuff repair, postoperative Bankart procedures and soft tissue strains and repairs. The sling includes a support pillow abuts the wearer's torso, and a pouch that receives the wearer's arm. A plurality of straps suspend the pillow and pouch from the wearer's non-treatment shoulder. One of the straps prevents the pillow from shifting relative to the user, thus securely maintaining the wearer's arm at desired angles of abduction and external rotation. The pillow further includes an attached exercise grip and an indicator line that aids a physician in properly fitting the sling to the wearer.

15 Claims, 8 Drawing Sheets

U.S. PATENT DOCUMENTS

| | | | |
|---|---|---|---|
| 5,383,844 | A | 1/1995 | Munoz et al. |
| 5,407,420 | A | 4/1995 | Bastyr et al. |
| 5,407,430 | A * | 4/1995 | Peters .................. 604/104 |
| 5,413,552 | A | 5/1995 | Iwuala |
| 5,423,333 | A | 6/1995 | Jensen et al. |
| 5,464,383 | A | 11/1995 | Padden et al. |
| 5,569,172 | A | 10/1996 | Padden et al. |
| 5,665,058 | A | 9/1997 | Young |
| 5,772,617 | A | 6/1998 | Lay |
| D396,291 | S | 7/1998 | Bakes |
| 5,792,083 | A * | 8/1998 | Joslin ........................ 602/4 |
| 5,830,165 | A | 11/1998 | Rowe et al. |
| 6,007,500 | A * | 12/1999 | Quintinskie, Jr. .......... 601/5 |
| 6,113,562 | A * | 9/2000 | Bonutti et al. ............ 602/20 |
| 6,659,971 | B2 * | 12/2003 | Gaylord ..................... 602/4 |
| 7,189,213 | B1 * | 3/2007 | Weber ....................... 602/20 |
| 2003/0135141 | A1 | 7/2003 | Berhorst |
| 2004/0129278 | A1 * | 7/2004 | Itoi ............................ 128/892 |

FOREIGN PATENT DOCUMENTS

| | | | |
|---|---|---|---|
| EP | 0904752 A | | 3/1999 |
| FR | 2771625 A | | 6/1999 |
| JP | 2001-299789 | * | 10/2001 |
| JP | 2003068426 A | * | 3/2003 |

OTHER PUBLICATIONS

Author Unknown, DonJoy Shoulder Stabilizer Developed with Dr. Tom Sawa, DonJoy™ advertisement, 1 page (front and back), Feb. 2002.

Author Unknown, Quadrant By DonJoy shoulder brace, Smith & Nephew DonJoy, Inc. catalog, 2 pages, Mar. 1995.

Author Unknown, Humeral Stabilizing System, Smith & Nephew DonJoy, Inc. catalog, 2 pages, Mar. 1992.

Author Unknown, The S.C.O.I. Shoulder Brace, Smith & Nephew DonJoy, Inc. catalog, 1 page, Jun. 1990.

Itoi et al., Position of Immobilization After Dislocation of the Glenohumeral Joint, The Journal of Bone and Joint Surgery, May 2001, pp. 661-667, vol. 83-A, No. 5.

Breg, Inc., Product Brochure, Neutral Wedge, date unknown, 2 pages.

Scott Kober, Upper Extremity—Patients Immobilized in External Rotation Avoid Recurrent Dislocations, Orthopedics Today—Online Newspaper, Mar. 2003, 3 pages.

* cited by examiner

SHOULDER SLING WITH SUPPORT PILLOW AND POUCH

BACKGROUND OF THE INVENTION

1. Field of the Invention

The present invention relates to orthopedic devices. More particularly, the present shoulder sling provides stable and secure support to a wearer's arm at a variety of angles of abduction and external rotation.

2. Description of the Related Art

Physicians frequently treat many shoulder ailments with shoulder slings. For example, following a shoulder dislocation or shoulder surgery, a physician may place the patient's affected arm in a sling so that the shoulder remains motionless while it heals. Many simple slings comprise just a pouch that is supported by a strap around the wearer's neck. The wearer's forearm rests within the pouch such that the elbow is at a 90° angle and the forearm extends across the wearer's abdomen. U.S. Pat. Nos. 4,372,301, 4,622,961 and 4,834,082 provide examples of such simple slings.

For certain shoulder treatments it is advantageous for the patient to maintain his or her shoulder at certain angles of abduction, extension and rotation. For these treatment situations, a physician frequently employs a sling that includes an elevation support device. The elevation support device maintains the wearer's arm at the desired angles, while straps and/or a pouch maintain the position of the wearer's arm relative to the support device.

U.S. Pat. No. 5,334,132 discloses an arm sling including a forearm support section 22 that is supported by a shoulder strap 18 and a waist strap 20. The forearm support section 22 includes a pocket 50 on a side facing the wearer. The pocket 50 encloses a foam cushion 52 that abuts the patient's waist and maintains the wearer's arm at a small abduction angle.

U.S. Pat. No. 4,598,701 discloses a shoulder abduction splint comprising a unitary block of synthetic foam material that supports the wearer's arm at a desired abduction angle. A plurality of straps 24, 26, 28, 29 support the block. The block includes a flat surface C that abuts the wearer, and a second surface B that supports the wearer's arm at approximately 45° of abduction. The block further includes a flat lower surface A. When the block is inverted, the lower surface A supports the wearer's arm at approximately 90° of abduction.

Current shoulder slings, including those slings described above, provide inadequate restraint against undesired shifting or rotation of the sling relative to the wearer. With each of these slings, generally a plurality of straps suspend the arm support portion from the wearer's neck and/or shoulders. These straps function only to retain the arm support portion at a desired height. If a strap is provided that wraps around the wearer's torso, this strap functions only to prevent the wearer's arm from reaching a greater abduction angle. None of the straps are properly positioned or tensioned to prevent other shifting of the wearer's arm that causes changes in the angles of extension and rotation. Such undesired shifting can lessen the effectiveness of the sling at treating the wearer's shoulder.

Current shoulder slings also do not support a wearer's arm at positive angles of external rotation. Some slings suspend the wearer's arm at 0° of abduction and 0° of rotation. Some suspend the wearer's arm at 0° of abduction and a positive angle of internal rotation. Finally, some suspend the wearer's arm at a positive angle of abduction and 0° of rotation.

Therefore, a shoulder sling that supports a wearer's arm at positive angles of external rotation, and that restrains the wearer's shoulder against undesired extension and rotation would be of great benefit to people with shoulder ailments.

SUMMARY OF THE INVENTION

The preferred embodiments of the present shoulder sling have several features, no single one of which is solely responsible for their desirable attributes. Without limiting the scope of this shoulder sling as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include positive restraint of the wearer's arm at desired angles of abduction and external rotation.

A preferred embodiment of the present shoulder sling supports a wearer's arm at desired angles of abduction and external rotation. The sling comprises a support pillow including a contoured medial surface for abutting the wearer's torso, and a lateral surface for operatively contacting and supporting the wearer's arm. A pouch receives and at least partially encloses the wearer's forearm. A plurality of straps secures the support pillow and the pouch to the wearer. A distance between anterior edges of the medial and lateral surfaces is substantially greater than a distance between posterior edges of the medial and lateral surfaces.

Another preferred embodiment of the present shoulder sling supports a wearer's arm at desired angles of abduction and external rotation. The sling comprises a support pillow including a lateral surface for operatively contacting and supporting the wearer's arm. A pouch secured to the support pillow lateral surface receives and at least partially encloses the wearer's forearm. A plurality of straps secure the support pillow and the pouch to the wearer. A first one of the straps comprises a chest strap that extends from an anterior surface of the support pillow to an anterior edge of a shoulder pad. A second one of the straps comprises a back strap that extends from a posterior edge of the pouch to a posterior edge of the shoulder pad. A third one of the straps comprises an anti-rotation strap that extends from an anterior edge of the shoulder pad to the support pillow adjacent a medial surface thereof.

Another preferred embodiment of the present shoulder sling supports a wearer's arm at desired angles of abduction and external rotation. The sling comprises a support pillow including a contoured medial surface for abutting the wearer's torso, and a lateral surface for operatively contacting and supporting the wearer's arm. A pouch receives and at least partially encloses the wearer's forearm. A plurality of straps secure the support pillow and the pouch to the wearer. An upper surface of the support pillow includes a straight indicator line that provides a visual cue to the wearer so that the wearer knows when the sling is properly fitted.

Another preferred embodiment of the present shoulder sling supports a wearer's arm at desired angles of abduction and external rotation. The sling comprises a support pillow including a contoured medial surface for abutting the wearer's torso, and a lateral surface for operatively contacting and supporting the wearer's arm. A pouch receives and at least partially encloses the wearer's forearm. A plurality of straps secure the support pillow and the pouch to the wearer. An anterior portion of the support pillow includes an attached exercise grip.

BRIEF DESCRIPTION OF THE DRAWINGS

The preferred embodiments of the present shoulder sling, illustrating its features, will now be discussed in detail. These embodiments depict the novel and non-obvious shoulder sling shown in the accompanying drawings, which are for illustrative purposes only. These drawings include the following figures, in which like numerals indicate like parts.

DETAILED DESCRIPTION OF THE PREFERRED EMBODIMENTS

Figure 1:
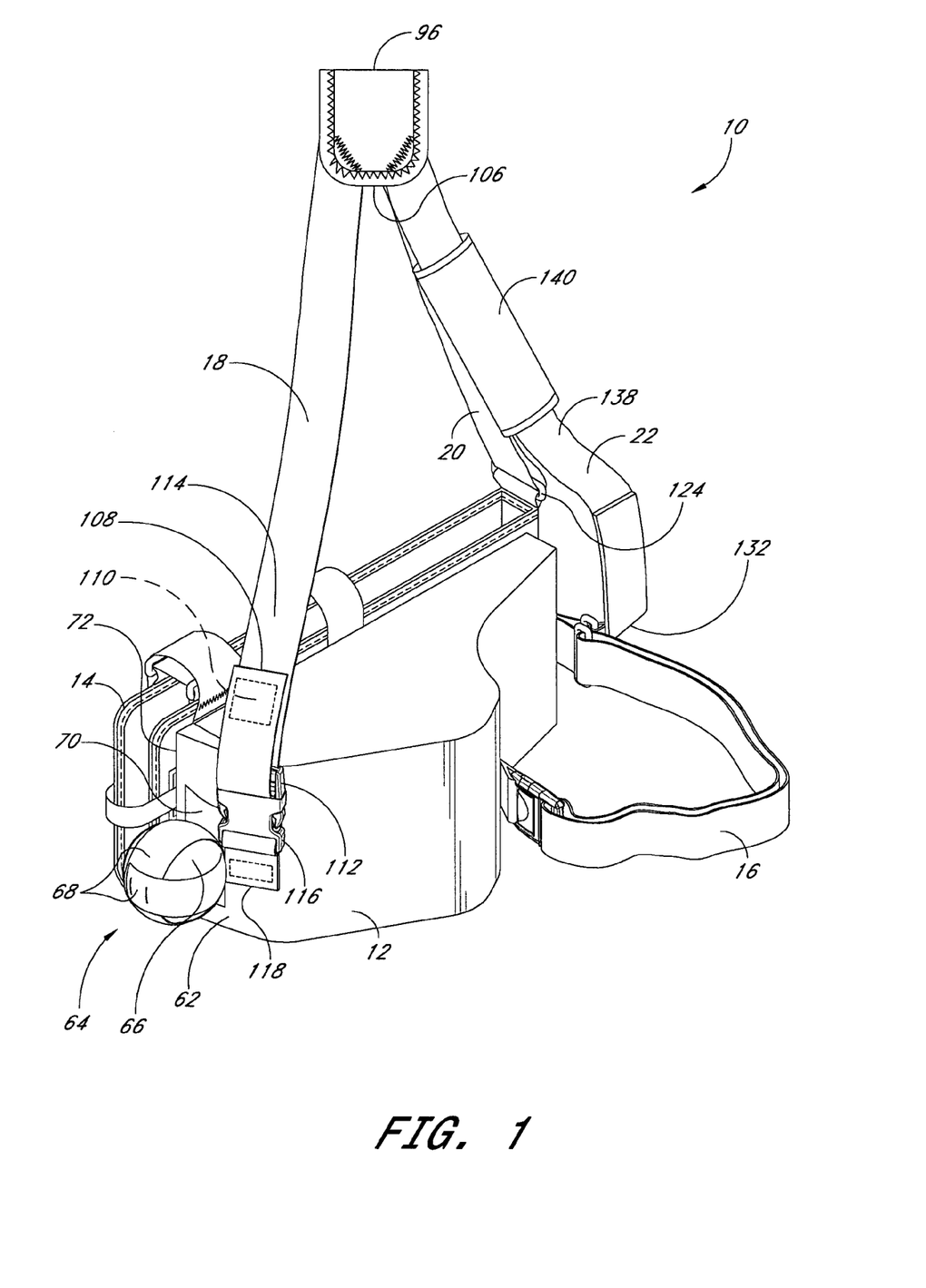
FIG. 1 is a front perspective view of a preferred embodiment of the present shoulder sling, illustrating a preferred support pillow.
Figure 2:
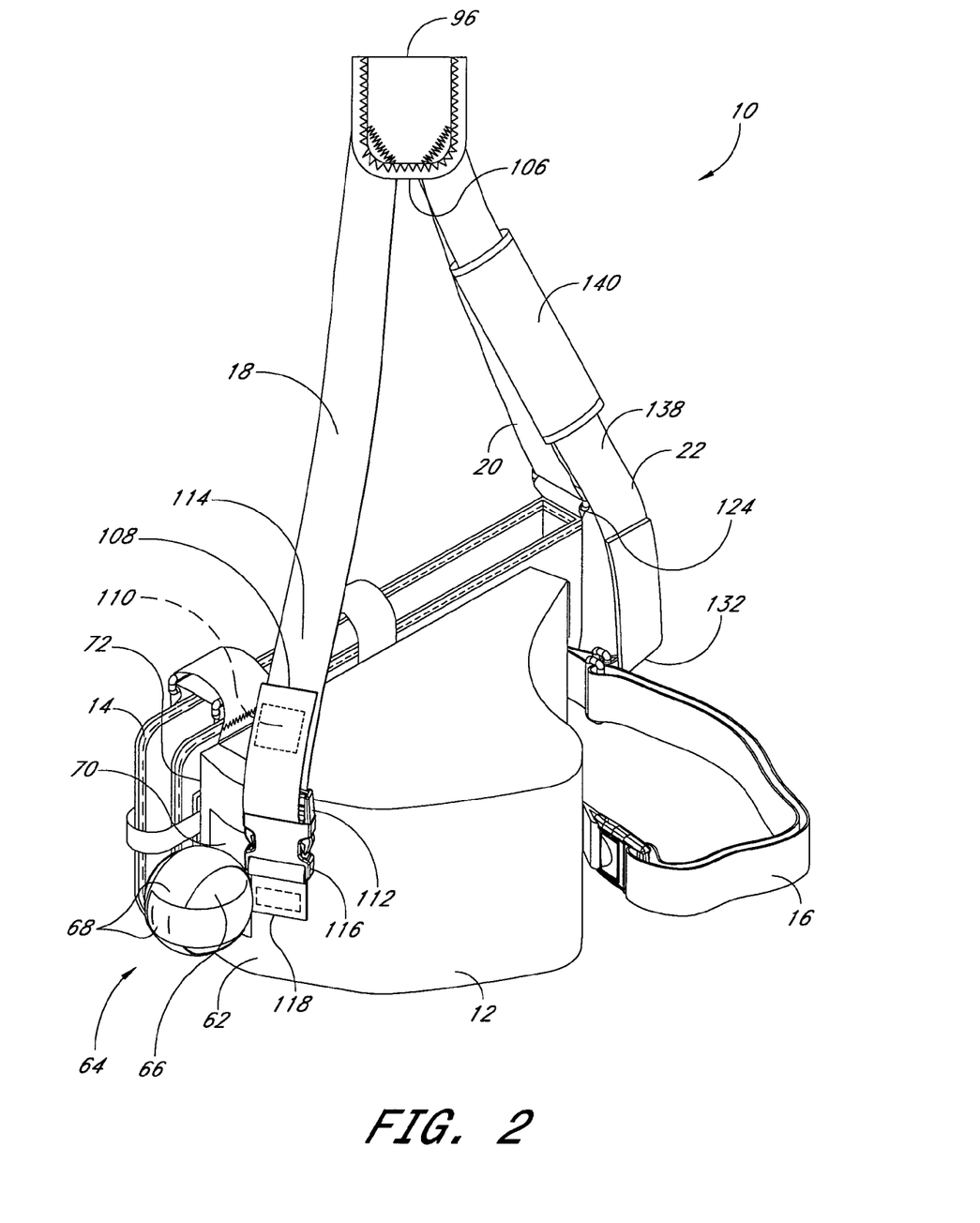
FIG. 2 is a front perspective view of another preferred embodiment of the present shoulder sling, illustrating another preferred support pillow.

As illustrated in FIGS. 1 and 2, the present shoulder sling 10 comprises a support pillow 12, a forearm pouch 14 and a plurality of straps 16, 18, 20, 22 that secure the pillow 12 and pouch 14 to a wearer. The sling 10 is particularly effective at treating gleno-humeral dislocations and subluxations, and capsular shifts. The sling 10 is also particularly effective for postoperative rotator cuff repair, postoperative Bankart procedures and soft tissue strains and repairs. The sling 10 maintains the wearer's arm at desired angles of abduction and external rotation.

In a particularly preferred embodiment, the sling 10 is capable of maintaining the wearer's arm at approximately 15° of abduction and approximately 15° of external rotation. In another particularly preferred embodiment, the sling 10 is capable of maintaining the wearer's arm at approximately 15° of abduction and approximately 30° of external rotation. Those of skill in the art will appreciate, however, that the sling 10 is capable of maintaining the wearer's arm at virtually any angle of abduction, extension or rotation. The magnitude of each of these angles depends upon the size and shape of the wearer, the size and shape of the support pillow 12 and the lengths of the straps 16, 18, 20, 22. FIGS. 1 and 2 illustrate differently sized and shaped support pillows 12. The pillow 12 of FIG. 1 maintains the wearer's arm at a smaller angle of external rotation, and the pillow 12 of FIG. 2 maintains the wearer's arm at a larger angle of external rotation.

Advantageously, the present sling 10 can be used to treat either the wearer's right or left shoulder. The Figures illustrate the sling 10 in a right-handed configuration. The sling 10 is easily converted to a left-handed configuration by detaching the straps 16, 18, 20, 22 and the forearm pouch 14 from the pillow 12, flipping the pillow over 12 so that it is adapted to rest against the wearer's left side, and reattaching the straps 16, 18, 20, 22 and the forearm pouch 14 to the pillow 12.

Figure 3:
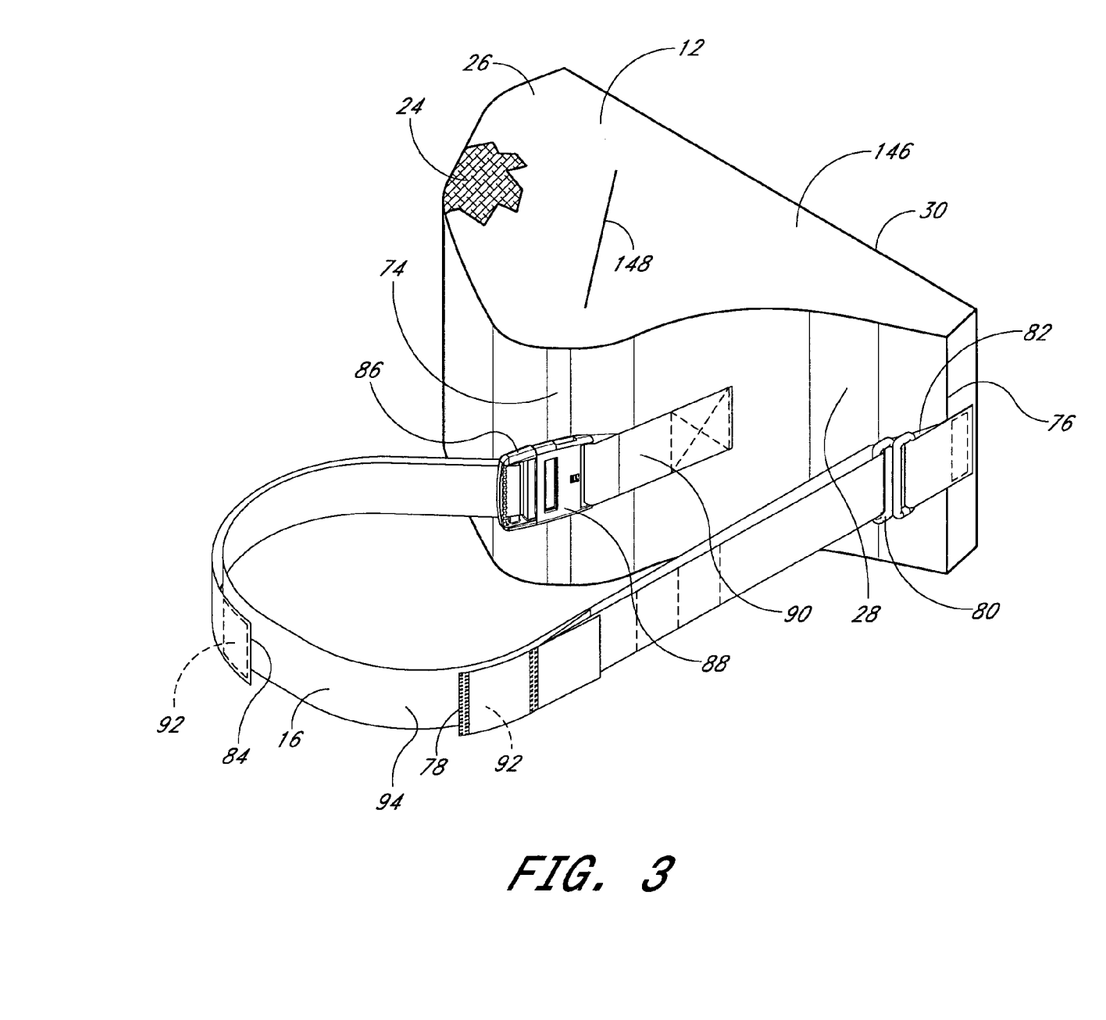
FIG. 3 is a rear perspective view of the support pillow and torso strap of FIG. 2.

With reference to FIG. 3, the support pillow 12 comprises a block 24 of lightweight material, such as foam. Preferably, the support pillow material is soft and resilient to provide greater comfort to the wearer. Preferably, an outer surface 26 of the pillow 12 comprises a loop material. For example, the pillow 12 may include a fabric cover 26 over a foam core 24, and the cover 26 may have a looped outer surface. The pillow outer surface 26 thus readily receives and releasably secures hook material, as described below. A preferred material for the fabric cover 26 is brushed nylon.

Figure 6:
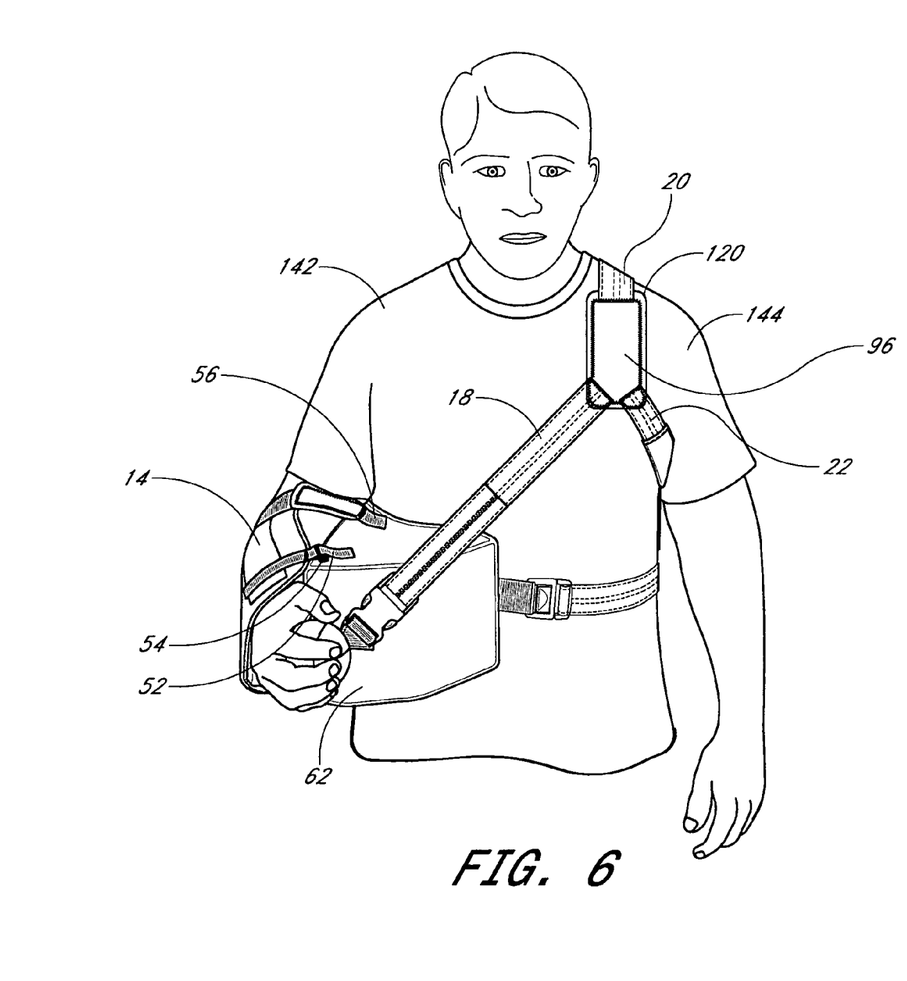
FIG. 6 is a front elevational view of the shoulder sling of FIG. 1, illustrating the sling properly applied to a wearer.
Figure 7:
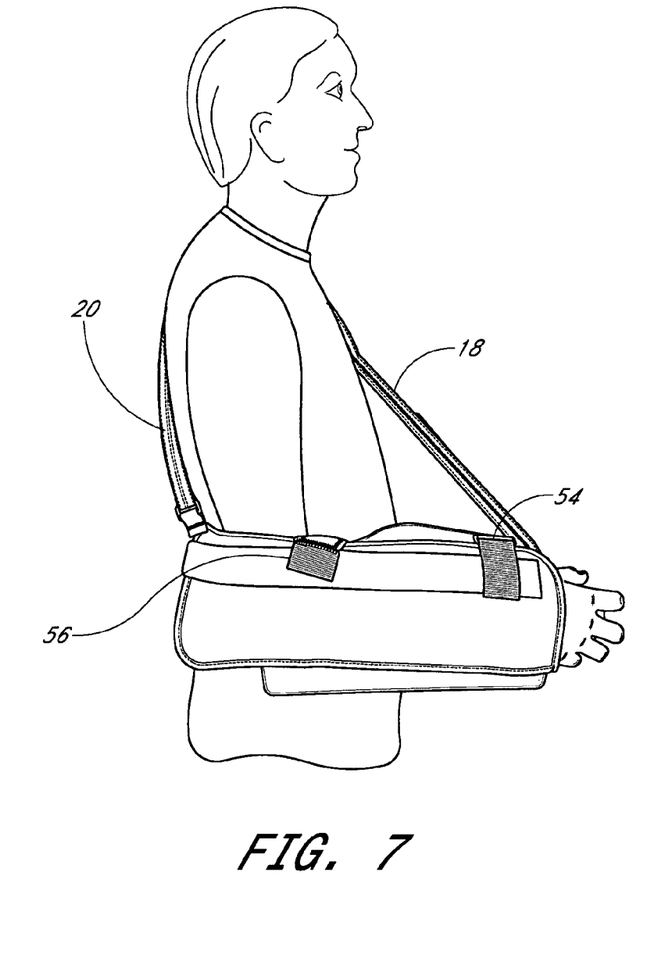
FIG. 7 is a left-side elevational view of the shoulder sling and wearer of FIG. 6.
Figure 8:
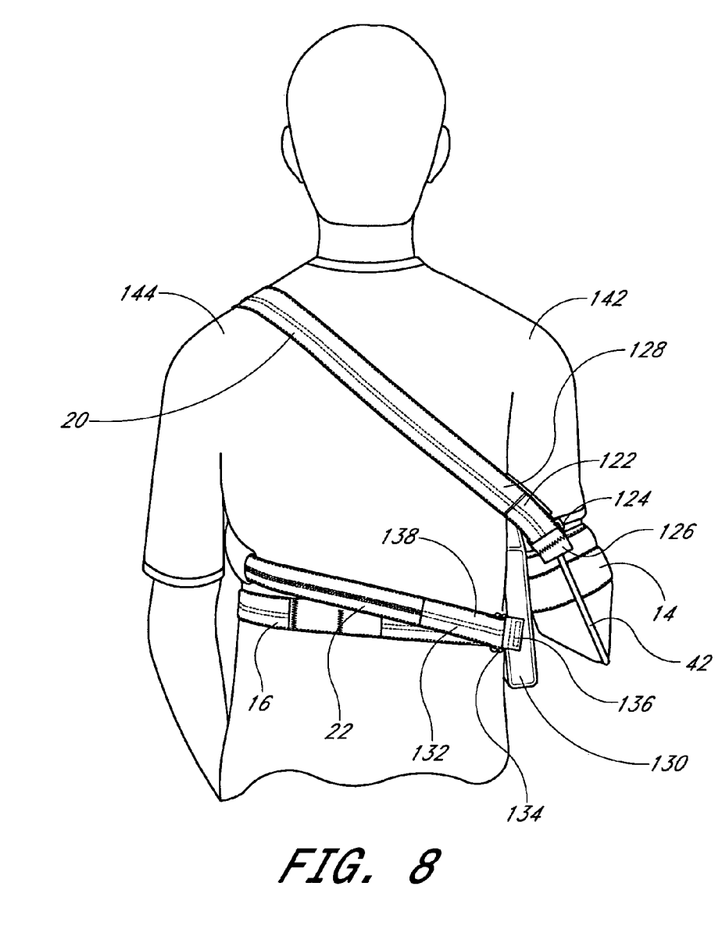
FIG. 8 is a rear elevational view of the shoulder sling and wearer of FIG. 6.

A medial surface 28 (FIG. 3) of the pillow 12 is contoured to abut and comfortably conform to the wearer's hip and torso, as illustrated in FIGS. 6-8. A lateral surface 30 of the pillow 12 is flat and abuts the forearm pouch 14, as illustrated in FIGS. 1 and 2. The relative positions and orientations of the medial surface 28 and the lateral surface 30 determine the angles of abduction and external rotation that the wearer's arm occupies when the sling 10 is worn.

Figure 5:
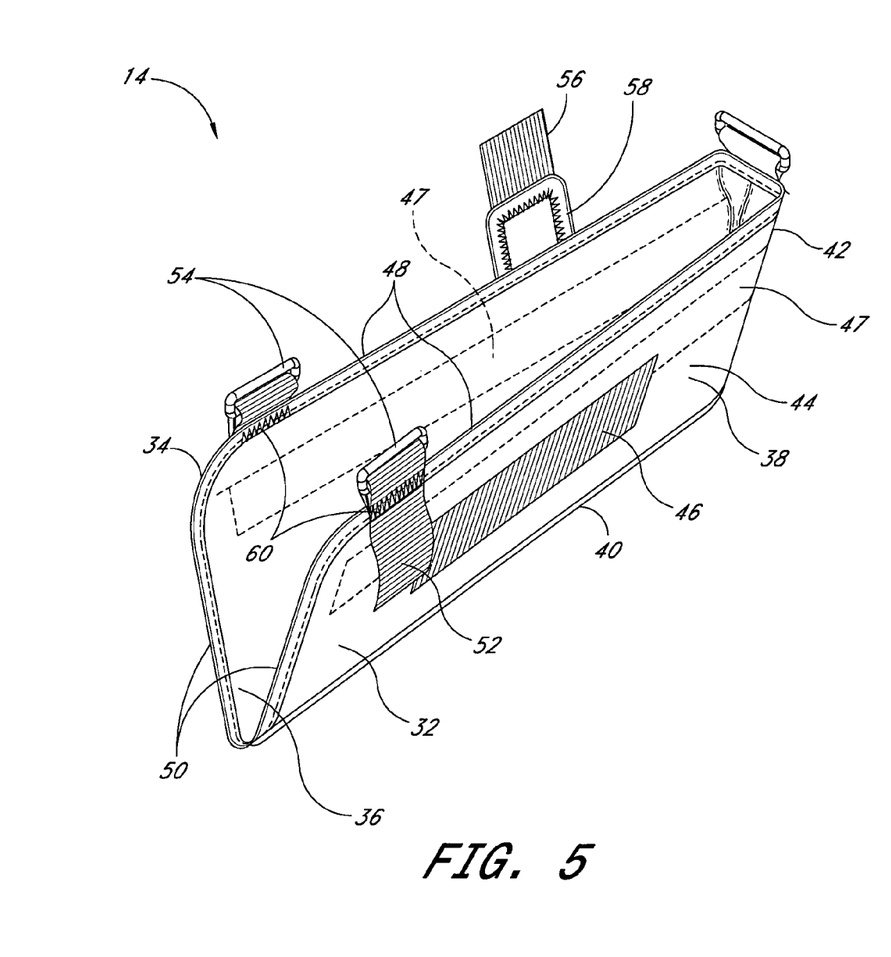
FIG. 5 is a front perspective view of the forearm pouch of FIGS. 1 and 2.

With reference to FIG. 5, in the right-handed configuration of the sling 10, the forearm pouch 14 comprises a medial panel 32 and a lateral panel 34. In the left-handed configuration (not shown) of the sling 10, the medial panel 32 is actually positioned laterally, and the lateral panel 34 is actually positioned medially. For ease of reference, the panels 32, 34 will be referred as they are positioned when the sling 10 is in the right-handed configuration.

The forearm pouch 14 is preferably constructed of materials that provide the pouch 14 with both some rigidity and some flexibility. For example, in a preferred embodiment the medial and lateral panels 32, 34 are each constructed of a laminate comprising a first outer layer of fabric, an inner layer of foam, and a second outer layer of fabric.

An inside surface 36 of the panels 32, 34 (the surface that contacts the wearer's arm) is preferably a soft, moisture absorbing material, such as a cotton-polyester blend. An outside surface 38 of the panels 32, 34 is preferably a durable material that is adapted to receive a hook material. For example, the outside surface 38 may be made of brushed nylon.

With further reference to FIG. 5, the medial and lateral panels 32, 34 are secured to each other along their respective lower edges 40 and posterior edges 42. The panels 32, 34 may be formed from a single sheet that is folded in half. The fold line may form either the lower edge 40 or the posterior edge 42 of the pouch 14. Alternatively, the panels 32, 34 may be formed of two separate sheets that are secured to one another along two edges. In the illustrated embodiment, the panels 32, 34 are formed from a single folded sheet, and the fold line forms the lower edge 40 of the pouch 14. Stitching (not shown) secures the posterior edges 42 of the panels 32, 34 together. Those of skill in the art will appreciate that edges 40, 42 of the panels 32, 34 could be secured to one another with a variety of alternate means, including both permanent and releasable means. Preferably, a medial surface 44 of the lateral panel 34 includes a patch of hook material 46. The hook material 46 engages the loop material on the pillow outer surface 26 to releasably secure the forearm pouch 14 to the pillow lateral surface 30, as shown in FIGS. 1 and 2. Outer surfaces of the pouch 14 may include strips of a loop material 47 (represented by dotted lines) having a different texture from the remainder of the pouch 14.

Upper edges 48 and anterior edges 50 of the panels 32, 34 are not secured to one another. When the sling 10 is worn, the wearer places his forearm in the pouch 14 as shown in FIGS. 6-8. The wearer's upper arm protrudes upwardly from the posterior portion of the pouch 14 (FIG. 7). The wearer's hand protrudes anteriorly from the anterior edges 50 of the pouch 14.

With reference to FIG. 5, a first strap 52 is secured to an anterior portion of the upper edge 48 of the medial panel 32 via a first D-ring 54. A second D-ring 54 is secured to an anterior portion of the upper edge 48 of the lateral panel 34. A second strap 56 is secured to a posterior portion of the upper edge 48 of the lateral panel 34. The second strap 56 includes an elastic portion 58.

In the illustrated embodiment, stitching 60 (FIG. 5) permanently secures the D-rings 54 to the panels 32, 34, and hook material (not shown) releasably secures the second strap 56 to the panel 34 (FIG. 7). However, those of skill in the art will appreciate that the D-rings 54 could be secured to the panels by alternate means. For example, the D-rings 54 could be secured to straps 58 (FIG. 7) that include hook material, and the hook material could be releasably securable to the outer surfaces of the pouch 14. Similarly, the strap 56 could be permanently secured to the panel 34, for example, by stitching.

As shown in FIGS. 5, 6 and 7, the strap 52 threads through the D-ring 54 on the panel 34 and folds back toward the pillow 12. Hook material on the strap 52 engages the loop material on the pillow 12 and secures the strap 52 to the pillow. Similarly, the strap 56 extends across the upper edges 48 of the panels 32, 34 toward the pillow 12. Hook material on the strap 56 engages the loop material on the pillow 12 and secures the strap 56 to the pillow. The elastic portion 58 of the strap 56 enables the strap 56 to stretch so that it may engage the pillow 12 at a variety of locations. The straps 52, 56 thus cinch the upper edges 48 of the pouch 14 together about the wearer's arm, as shown in FIGS. 6 and 7.

With reference to FIGS. 1 and 2, an anterior surface 62 of the pillow 12 preferably includes an exercise grip 64. In the illustrated embodiment, the grip 64 comprises a spherical ball 66 of resilient and compressible material. Those of skill in the art will appreciate that the ball 66 could be any shape. First and second circular straps 68 secure the ball 66 to the pillow 12. The straps 68 are secured at the same location to a patch 70 of hook material. The hook material patch 70 engages the loop material on the pillow 12 to secure the straps 68 to the pillow 12. The grip 64 is thus securable to the pillow 12 at virtually any location. Those of skill in the art will appreciate that the grip 64 could be attached to the pillow 12 in other ways, such as by stitching that would permanently secure the grip 64 to the pillow 12 in one location.

The circular straps 68 are offset from one another by 90°. The straps 68 thus surround the majority of the surface of the ball 66, preventing it from accidentally escaping from the straps 68. To place the ball 66 within the straps 68, or to remove the ball 66 from between the straps 68, the wearer pries apart two adjacent straps 68 and forces the compressible ball 66 through the gap created between the separated straps 68. Those of skill in the art will appreciate that the ball 66 could be secured with a different strap arrangement, such as with one circular strap and one semi-circular strap that is offset from the circular strap by 90°.

In the illustrated embodiment, the grip 64 advantageously attaches to the pillow 12 adjacent an edge 72 of the pillow 12 that divides the anterior surface 62 and the lateral surface 30. When the sling 10 is worn, the grip 64 is located where the wearer can easily reach it with the hand on his or her treatment arm, as shown in FIG. 6. The wearer can thus use the exercise grip 64 without removing it from the straps 68. Of course, if desired the wearer can remove the exercise grip 64 from the straps 68 before exercising his or her hand with it.

With reference to FIG. 3, a torso strap 16 extends between an anterior edge 74 and a posterior edge 76 of the pillow medial surface 28. The torso strap 16 wraps around the wearer's torso, as shown in FIGS. 6 and 8, and secures the support pillow 12 to the wearer. A posterior end 78 of the strap preferably threads through a D-ring 80 that is permanently secured via a strap 82 to the pillow 12 adjacent the posterior edge 76 of the medial surface 28. An anterior end 84 of the torso strap 16 preferably threads through a first buckle portion 86. The first buckle portion 86 releasably engages a second buckle portion 88 that is permanently secured via a strap 90 to the pillow 12 adjacent the anterior edge 74 of the medial surface 28.

Each end 78, 84 of the torso strap 16 includes hook material 92. Intermediate portions 94 of the torso strap 16 include loop material (not shown). The posterior and anterior ends 78, 84 of the torso strap 16 thread through the D-ring 80 and the first buckle portion 86, respectively, and fold back onto the intermediate portions 94 of the torso strap 16. The hook surfaces 92 on the ends matingly engage the loop surfaces at the intermediate portions 94. A length of the torso strap 16 may thus be adjusted by varying the points at which the ends 78, 84 engage the intermediate portions 94. Those of skill in the art will appreciate that the ends 78, 84 could include loop material and the intermediate portions 94 could include hook material.

Figure 4:
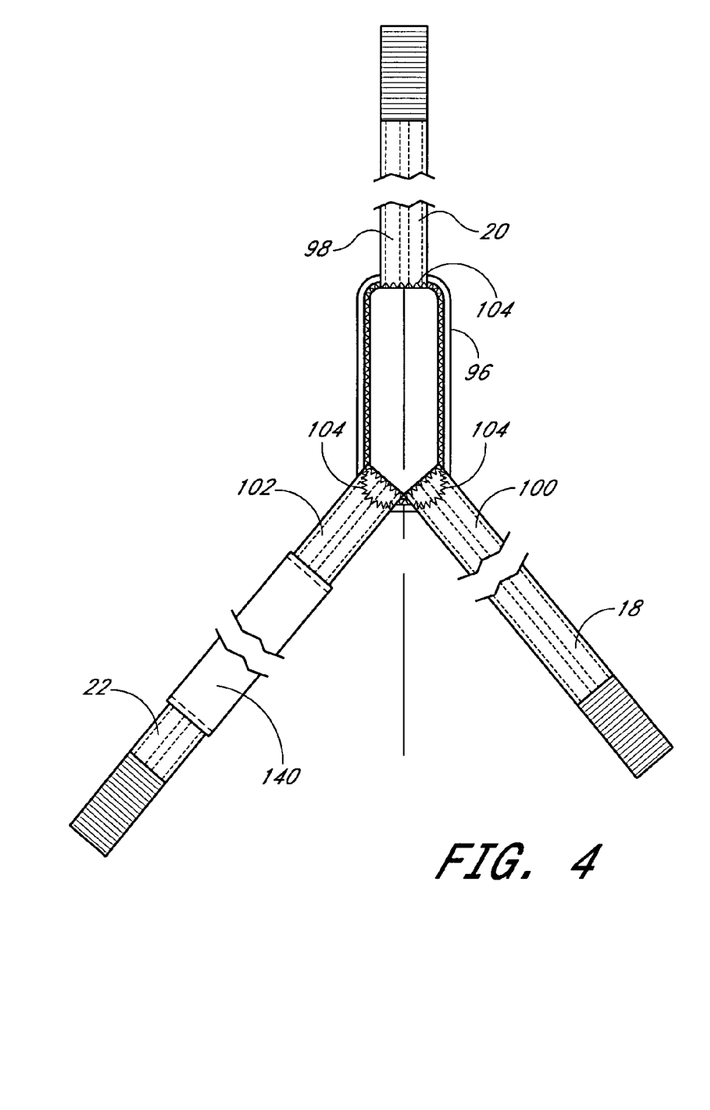
FIG. 4 is a bottom plan view of the shoulder pad, chest strap, back strap and anti-rotation strap of FIGS. 1 and 2.

With reference to FIG. 4, a plurality of straps 18, 20, 22 engage a shoulder pad 96 and suspend the sling 10 from the wearer's non-treatment shoulder, as shown in FIGS. 6-8. In the illustrated embodiment, the shoulder pad 96 is positioned over the wearer's chest. Depending upon the wearer's preference, the shoulder pad 96 may be positioned over the wearer's shoulder, such that part of the pad 96 extends anteriorly from the wearer's shoulder, and part of the pad 96 extends posteriorly from the wearer's shoulder.

The straps 18, 20, 22 preferably are constructed of a flexible and durable material, such as nylon fabric. The shoulder pad 96 preferably comprises a strip of a cushioning and resilient material, and may comprise multiple layers. For example, the pad may comprise an inner layer of springy foam material covered by an outer layer of a durable fabric, such as nylon. In the illustrated embodiment, the pad 96 is rectangular. However, those of skill in the art will appreciate that the shoulder pad 96 could be any shape.

In the illustrated embodiment, upper ends 98, 100, 102 of the straps 18, 20, 22 are permanently secured to the shoulder pad 96 by stitching 104. Those of skill in the art will appreciate that the straps 18, 20, 22 could be secured to the shoulder pad 96 by a variety of alternate means. For example, hook and loop material could releasably secure the straps 18, 20, 22 to the shoulder pad 96.

With reference to FIGS. 1 and 2, a chest strap 18 extends from an anterior edge 106 of the shoulder pad 96 downward to the anterior surface 62 of the support pillow 12. A lower end 108 of the chest strap 18 includes hook material 110. The lower end 108 of the strap 18 threads through a first buckle portion 112 and folds back over onto an intermediate portion 114 of the chest strap 18. The intermediate portion 114 includes loop material (not shown). The end 108 is thus releasably securable to the intermediate portion 114 at a variety of locations so that a length of the chest strap 18 is adjustable. The first buckle portion 112 releasably engages a second buckle portion 116 that is permanently secured to the pillow anterior 62 surface via a strap 118.

With reference to FIGS. 6 and 8, a back strap 20 extends from a posterior edge 120 of the shoulder pad 96 downward to the posterior edge 42 of the arm pouch 14. A lower end 122 of the back strap 20 includes hook material (not shown). This end of the strap 20 threads through a D-ring 124 that is permanently secured to the upper posterior edge 42 of the pouch 14 via a strap 126. The end 122 folds back over onto an intermediate portion 128 of the back strap 20. The intermediate portion 128 includes loop material (not shown). The end 122 is thus releasably securable to the intermediate portion 128 at a variety of locations so that a length of the back strap 20 is adjustable.

With reference to FIGS. 1, 2, 6 and 8, an anti-rotation strap 22 extends from the anterior edge 106 of the shoulder pad 96 downward and around the wearer's torso to a posterior surface 130 (FIG. 8) of the support pillow 12. A lower end 132 of the anti-rotation strap 22 includes hook material (not shown). This end of the strap 22 threads through a D-ring 134 that is permanently secured to the pillow posterior surface 130 via a strap 136. The end 132 folds back over onto an intermediate portion 138 of the anti-rotation strap 22. The intermediate portion 138 includes loop material. The end 132 is thus releasably securable to the intermediate portion 138 at a variety of locations so that a length of the anti-rotation strap 22 is adjustable.

With reference to FIGS. 1, 2 and 4, the anti-rotation strap 22 preferably includes a padded sleeve 140. In the illustrated embodiment, the sleeve 140 comprises a rectangular pad that is folded in half and sewn to form a tube. Those of skill in the art will appreciate that the sleeve 140 could be formed in a variety of other fashions, such as by sewing together two rectangular pads along two edges. The sleeve 140 preferably comprises a cushioning and resilient material, and may comprise multiple layers. For example, the sleeve 140 may comprise an inner layer of springy foam material covered by an outer layer of a durable fabric, such as nylon.

The sleeve 140 provides a cushioning layer between the anti-rotation strap 22 and the wearer, thereby increasing the wearer's comfort while wearing the sling 10. The sleeve 140 is preferably slidable along the anti-rotation strap 22 so that the wearer may position the sleeve 140 in the most comfortable manner. For example, in FIGS. 6 and 8, the wearer has positioned the sleeve 140 so that it overlies the pectoral muscle and the ribs.

With reference to FIGS. 6 and 8, the anti-rotation strap 22 advantageously restricts the sling 10 from moving relative to the wearer. Any tendency of the pillow 12 to rotate about the wearer's torso creates tension in the anti-rotation strap 22 that tends to pull the pillow 12 in the opposite direction. For example, a force acting on the pillow 12 and tending to rotate it about the wearer toward the wearer's back creates tension in the chest strap 18 tending to pull the shoulder pad 96 toward the wearer's treatment shoulder 142. The force on the shoulder pad 96 creates tension in the anti-rotation strap 22 tending to pull the shoulder pad 96 back toward the wearer's non-treatment shoulder 144. Similarly, a force acting on the pillow 12 and tending to rotate it about the wearer toward the wearer's abdomen creates tension in the back strap 20 tending to pull the shoulder pad 96 toward the wearer's treatment shoulder 142. The force on the shoulder pad 96 creates tension in the anti-rotation strap 22 tending to pull the shoulder pad 96 back toward the wearer's non-treatment shoulder 144. The anti-rotation strap 22 thus enables the sling 10 to retain the wearer's arm at the desired angles of abduction and external rotation, which increases the effectiveness of the sling 10 in treating the wearer's shoulder 142.

FIGS. 6-8 illustrate the sling 10 fitted to a wearer. The support pillow 12 rests against the wearer's hip beneath the treatment shoulder 142. The pillow medial surface 28 abuts the wearer's hip and torso, and the wearer's forearm rests within the pouch 14. The shoulder pad 96 rests upon the wearer's non-treatment shoulder 144. The chest strap 18 extends from the shoulder pad 96 diagonally downward and across the wearer's chest to the anterior portion 62 of the support pillow 12. The back strap 20 extends from the shoulder pad 96 diagonally downward and across the wearer's back to the upper posterior edge 42 of the arm pouch 14. The anti-rotation strap 22 extends from the shoulder pad 96 diagonally downward and across the wearer's chest, around the wearer's torso underneath the non-treatment shoulder 144, and across the wearer's back to the posterior surface 130 of the support pillow 12.

Typically, a physician initially fits the sling 10 to the wearer. The sling 10 is preferably available in a variety of sizes to fit wearers of different sizes. After applying the proper size sling 10 to the wearer as shown in FIGS. 6-8, the physician adjusts the length of the torso strap 16 so that it fits snugly about the wearer's waist. The physician also adjusts the lengths of the chest, back and anti-rotation straps 18, 20, 22 until the straps 18, 20, 22 properly support the wearer's arm at the desired angles of abduction and external rotation.

With reference to FIG. 3, preferably, an upper surface 146 of the support pillow 12 includes a straight indicator line 148 that the physician can use to properly adjust the straps 18, 20, 22. The physician observes the orientation of the indicator line 148 as he or she fits the sling 10 on the wearer. When the line 148 is parallel to a medial-lateral axis of the wearer's body, the straps 18, 20, 22 are properly adjusted for the desired angle of external rotation. To aid the physician in properly aligning the sling 10, he or she may position the wearer so that he or she is facing a wall. The physician can then determine whether or not the indicator line 148 is parallel to the wall, and make strap adjustments as necessary. By positioning the wearer very close to the wall, the physician can even measure to verify that the distances between the wall and various points on the indicator line 148 are equal to one another, as they should be if the indicator line 148 is parallel to the wall.

Once the sling 10 has been properly fitted, the wearer may easily remove and reapply the sling 10 by himself or herself. To remove the sling 10, the wearer simply disconnects the first and second buckle portions on the torso strap 16 and the chest strap 18. Gravity pulls the support pillow 12 toward the ground, and the entire sling 10 is suspended from the wearer's non-treatment shoulder 144 by the shoulder pad 96. The wearer then grasps the shoulder pad 96 and pulls his or her non-treatment arm through the space between the back strap 20 and the anti-rotation strap 22.

To quickly and easily apply the sling 10, the wearer begins with the first and second buckle portions 112, 116 of the chest strap 18 disconnected and the first and second buckle portions 86, 88 on the torso strap 16 disconnected. The torso strap 16, back strap 20 and the anti-rotation strap 22 are each connected to their respective D-rings. The wearer places his or her arm in the pouch 14 and secures the straps 52, 56. Next, the wearer positions the pillow 12 on the side of his or her body beneath the treatment shoulder 142 and secures the pillow 12 with the torso strap 16 by reconnecting the first and second buckle portions 86, 88. The wearer inserts his or her non-treatment arm 144 into the opening between straps 20, 22 and positions the pad 96 on the shoulder 144. Finally, the wearer secures the chest strap 18 by connecting the first and second buckle portions 112, 116.

SCOPE OF THE INVENTION

The above presents a description of the best mode contemplated for carrying out the present shoulder sling, and of the manner and process of making and using it, in such full, clear, concise, and exact terms as to enable any person skilled in the art to which it pertains to make and use this shoulder sling. This shoulder sling is, however, susceptible to modifications and alternate constructions from that discussed above that are fully equivalent. Consequently, this shoulder sling is not limited to the particular embodiments disclosed. On the contrary, this shoulder sling covers all modifications and alternate constructions coming within the spirit and scope of the shoulder sling as generally expressed by the following claims, which particularly point out and distinctly claim the subject matter of the shoulder sling.

What is claimed is:

1. A shoulder sling for supporting a wearer's arm at desired angles of abduction and external rotation, the sling comprising:
   a support pillow including a contoured medial surface for abutting the wearer's torso, and a lateral surface for operatively contacting and supporting the wearer's arm;
   a pouch for receiving and at least partially enclosing the wearer's forearm; and
   a plurality of straps for securing the support pillow and the pouch to the wearer; wherein
   a distance between anterior edges of the medial and lateral surfaces is substantially greater than a distance between posterior edges of the medial and lateral surfaces, wherein one of the plurality of straps comprises an anti-rotation strap that extends from an anterior edge of a shoulder pad to the support pillow adjacent the posterior edge of the medial surface.

2. The shoulder sling of claim 1, wherein the support pillow retains the wearer's arm in a position of approximately 15° of abduction and approximately 15° of external rotation.

3. The shoulder sling of claim 1, wherein the support pillow retains the wearer's arm in a position of approximately 15° of abduction and approximately 30° of external rotation.

4. The shoulder sling of claim 1, wherein one of the straps comprises a torso strap that extends from the support pillow adjacent the anterior edge of the medial surface to the support pillow adjacent the posterior edge of the medial surface.

5. The shoulder sling of claim 4, wherein another one of the straps comprises a chest strap that extends from an anterior surface of the support pillow to an anterior edge of the shoulder pad.

6. The shoulder sling of claim 5, wherein another one of the straps comprises a back strap that extends from a posterior edge of the pouch to a posterior edge of the shoulder pad.

7. The shoulder sling of claim 4, wherein the torso strap further comprises a buckle adapted to quickly secure the torso strap about the wearer's torso and quickly release the torso strap from the wearer's torso.

8. The shoulder sling of claim 1, wherein the pouch is releasably secured to the support pillow lateral surface.

9. The shoulder sling of claim 1, further comprising a resilient compressible member secured to an anterior surface of the support pillow.

10. The shoulder sling of claim 1, wherein:
    an upper surface of the support pillow includes a straight indicator line that provides a visual cue to the wearer so that the wearer knows when the sling is properly fitted.

11. The shoulder sling of claim 10, wherein the straight indicator line is positioned and oriented to provide the visual cue to the wearer when the wearer has the pillow properly fitted and positioned so as to maintain the wearer's arm in a position of external rotation.

12. The shoulder sling of claim 11, wherein the straight indicator line is arranged to be generally parallel to an orthogonal direction relative to the wearer's body when the sling is properly fitted so as to maintain the wearer's arm in the position of external rotation.

13. The shoulder sling of claim 12, wherein the orthogonal direction is a medial-lateral axis of the wearer's body.

14. The shoulder sling of claim 1, wherein the shoulder pad cooperates with at least one of the plurality of straps to suspend the support pillow from the wearer's shoulder.

15. The shoulder sling of claim 1, wherein the support pillow is shaped and configured such that when the support pillow occupies a first orientation it is adapted to support the wearer's right arm, and when the support pillow is inverted from the first orientation it is adapted to support the wearer's left arm.

* * * * *